(12) United States Patent
Ruvinsky et al.

(10) Patent No.: US 6,653,146 B1
(45) Date of Patent: Nov. 25, 2003

(54) BIO-BURDEN VISUALIZATION SYSTEM

(75) Inventors: Lee Ruvinsky, Belle Mead, NJ (US); Bernard Esquenet, Old Brookville, NY (US); Marc Esquenet, Old Brookville, NY (US)

(73) Assignee: Chemclean Corporation, Springfield Gardens, NY (US)

( * ) Notice: Subject to any disclaimer, the term of this patent is extended or adjusted under 35 U.S.C. 154(b) by 119 days.

(21) Appl. No.: 09/713,666

(22) Filed: Nov. 15, 2000

Related U.S. Application Data

(60) Provisional application No. 60/165,605, filed on Nov. 15, 1999.

(51) Int. Cl.[7] .............................................. G01N 21/76
(52) U.S. Cl. ...................... 436/172; 436/63; 436/164; 422/82.08; 356/51; 250/461.1; 250/461.2
(58) Field of Search ........................ 436/63, 164, 165, 436/172; 422/82.05, 82.08, 24; 435/287.4, 288.7; 356/51; 600/310, 317; 250/459.1, 461.1, 461.2

(56) References Cited

U.S. PATENT DOCUMENTS

| | | | |
|---|---|---|---|
| 3,883,247 A | 5/1975 | Adams | 356/39 |
| 4,087,685 A | 5/1978 | Froot | 250/302 |
| 4,094,745 A | 6/1978 | Scholefield | 195/103.5 |
| 4,115,699 A | 9/1978 | Mizuta et al. | 250/461 B |
| 4,390,787 A | 6/1983 | Jennings et al. | 250/459.1 |
| 4,500,641 A | 2/1985 | van den Engh et al. | 435/291 |
| 4,565,790 A | 1/1986 | Hemmilä et al. | 436/537 |
| 4,621,193 A * | 11/1986 | Van Hoye | 250/302 |
| 4,698,308 A | 10/1987 | Ikeda | 435/291 |
| 4,800,282 A | 1/1989 | Nishimura | 250/461.1 |
| 4,812,393 A | 3/1989 | Goswami et al. | 435/4 |
| 4,858,465 A * | 8/1989 | Molina | 250/301 |
| 4,866,283 A | 9/1989 | Hill, Jr. | 250/461.2 |
| 4,938,224 A | 7/1990 | Rysavy | 128/633 |
| 5,474,910 A | 12/1995 | Alfano | 435/34 |
| 5,624,810 A | 4/1997 | Miller et al. | 435/8 |
| 5,701,012 A | 12/1997 | Ho | 250/461.2 |
| 5,807,605 A | 9/1998 | Tingey et al. | 427/8 |
| 5,863,790 A | 1/1999 | Bolea | 435/287.4 |
| 5,900,067 A * | 5/1999 | Jones | 134/1 |
| 6,083,755 A * | 7/2000 | Buess et al. | 134/1 |
| 6,107,097 A * | 8/2000 | Pfeifer | 435/13 |

FOREIGN PATENT DOCUMENTS

| | | | |
|---|---|---|---|
| DE | 29719497 | | 1/1998 |
| DE | 19633808 | * | 2/1998 |
| DE | 19649925 | * | 6/1998 |
| EP | 0347494 | | 12/1989 |
| EP | 0913681 | | 11/1998 |
| JP | 61164158 | * | 7/1986 |
| JP | 11281577 | * | 10/1999 |
| WO | WO 90/14591 | | 11/1990 |
| WO | WO 93/19152 | | 9/1993 |
| WO | WO 98/04682 | | 2/1998 |
| WO | WO 98/21569 | | 3/1998 |

OTHER PUBLICATIONS

Chu et al. American Journal of Infection Control. vol. 27 (4), pp. 315–319, Aug. 1999.*
Patent Abstracts of Japan, vol. 2000, No. 1 (JP 11 281577).
Ultraviolet Products Catalog, copyright 1999.

* cited by examiner

Primary Examiner—Maureen M. Wallenhorst
(74) Attorney, Agent, or Firm—Fitzpatrick, Cella, Harper & Scinto

(57) ABSTRACT

A method of visualizing biological material on medical instruments is disclosed which consists of the steps of selecting a dye material capable of creating fluorescence or phosphorescence when applied to biological material and subjected to ultraviolet light; applying the dye to a medical instrument; mounting the medical instrument in a viewing box; exposing the medical instrument in the viewing box to ultraviolet light and observing the instrument through an opening in the view box to determine if the dye has caused fluorescence or phosphorescence of material on the instrument indicative of the presence of biological material thereon.

13 Claims, 4 Drawing Sheets

(2 of 4 Drawing Sheet(s) Filed in Color)

BIO-BURDEN VISUALIZATION SYSTEM

This application claims the benefit of Provisional Application No. 60/165,605, filed Nov. 15, 1999.

BACKGROUND OF THE INVENTION

Field of the Invention

The present invention relates to a bio-burden visualization system, and more in particular, to a system and method for visualizing organic bio-burden residues on medical instruments.

It is of the utmost importance in the medical field that medical instruments, particularly surgical instruments, be carefully and completely cleaned prior to sterilization. After use, such instruments typically contain bio-burden residues of blood, fat, mucous, lipids, carbohydrates, protein or food residues which must be removed before sterilization. If such matter is not removed before sterilization they can harden and entrap bacteria protecting them from sterilization, therefore promoting cross contamination during subsequent procedures. That process does not remove such residue which remains on the instrument. The entrapped bacteria can contaminate a surgical site when the instrument is used again.

Normally, unaided visual inspection of a medical, "cleaned" device will usually not be able to detect bio-burden residue. Therefore, simple visual inspection does not ensure that proper cleaning has occurred and does not ensure that successful sterilization will take place.

In addition, despite the most careful cleaning, many surgical instruments, including orthopaedic and laproscopic instruments, as well as endoscopes and the like, are very difficult to clean. Therefore, it has been found desirable to visually ensure that such instruments are completely cleaned and all of the above-described bio-burden removed before sterilization. Alternatively, a sterilized instrument can be checked for bio-burden with the system of the present invention after sterilization and, if necessary, the instrument can then be re-cleaned and re-sterilized.

It is an object of the present invention to provide a bio-burden visualization system which is relatively simple to use and highly effective in allowing visualization of bio-burden remaining on surgical instruments.

Yet another object of the present invention is to provide a bio-burden visualization system which is reliable in use.

A further object of the present invention is to provide a bio-burden visualization system which is economical and yet has a high degree of accuracy.

In accordance with an aspect of the present invention, a bio-burden visualization system and method is provided which utilizes visualizing compounds or dyes that will affix to specific bio-burden residues and fluoresce or phosphoresce under appropriate conditions. These visualization compounds are generally in a liquid form which can be easily applied to an instrument by dipping or swabbing. However, solid or gas visualizing compounds may also be used.

The method of the present invention can be utilized to visualize bio-burden residues left on surfaces of surgical instruments, medical equipment and the like after cleaning or after sterilization. The system can also be used in a training program to test the quality of cleaning supplies and techniques used in the cleaning process. It could also be used for inspection, training and certification of cleanliness on food preparation surfaces.

The patent file contains drawings executed in color photographs. Copies of this patent with color photographs will be provided by the U.S. Patent and Trademark Office upon request and paymant of the necessary fee.

The above, and other objects, features and advantages of this invention will be apparent from the following detailed description of an illustrative embodiment thereof, which is to be read in connection with the accompanying drawings wherein.

Figure 1:
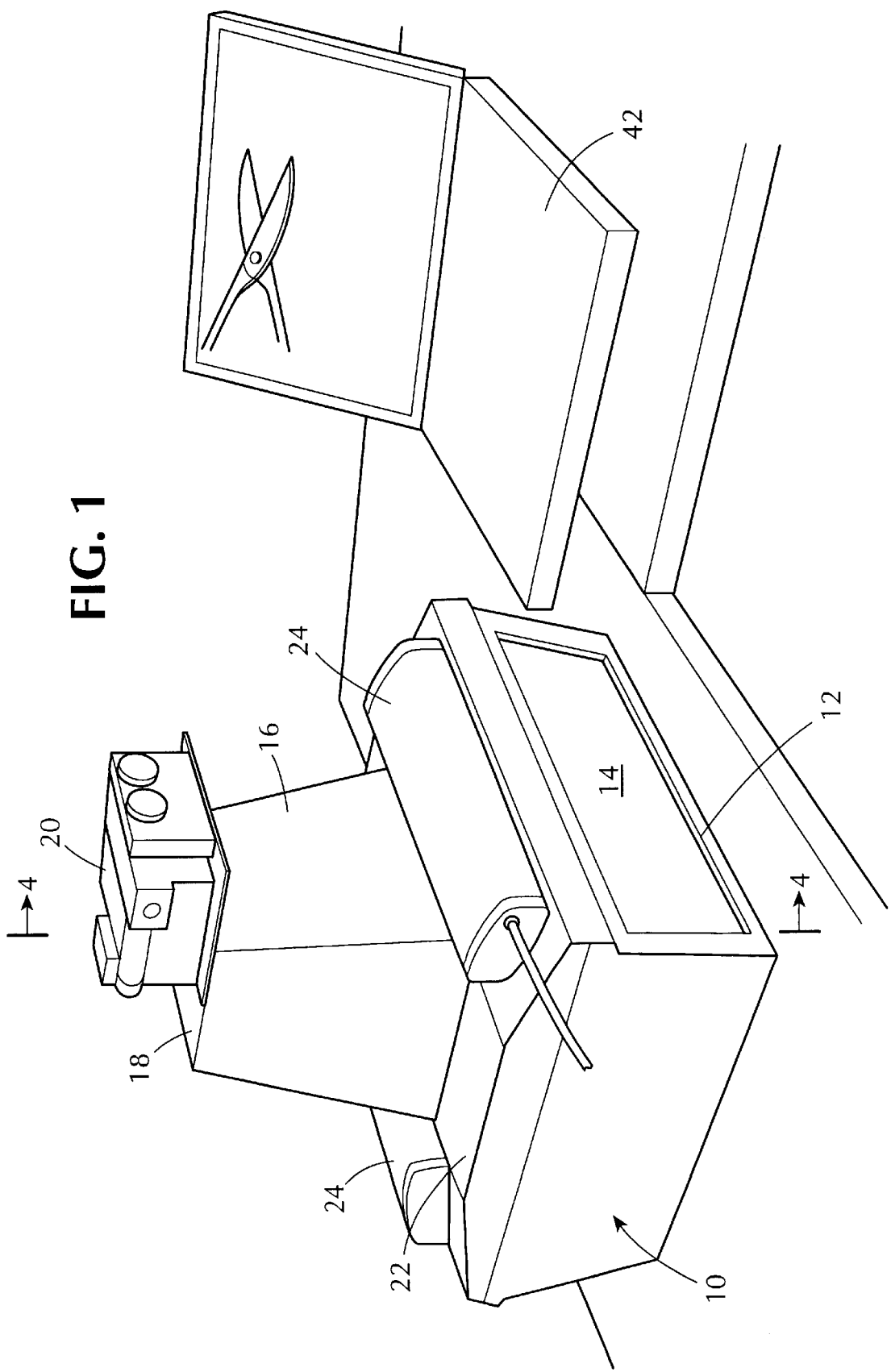
FIG. 1 is a perspective view of a device for use in the bio-burden visualization system and method of the present invention.

Referring now to the drawings in detail, and initially to FIG. 1, a viewing cabinet or housing 10 is illustrated in which visualization of bio-burden takes place according to the present invention. The housing consists of an enclosure having an open front end 12 which is closed by a flexible light shield 14 or the like, which allows access to the interior of the housing. The light shield as illustrated is a flexible sheet of black material, but could be a door or the like.

A camera support which is in the shape of frustro-pyramid 16 is mounted above an opening on the top of the housing and provides support at its upper end 18 for a camera 20. The camera may be a conventional photographic film camera or an electronic CCD camera of conventional construction. The upper surface 22 of housing 10 has ultraviolet light sources 24 mounted thereon, which project ultraviolet light through openings in top wall 22 to the interior of the housing.

Figure 4:
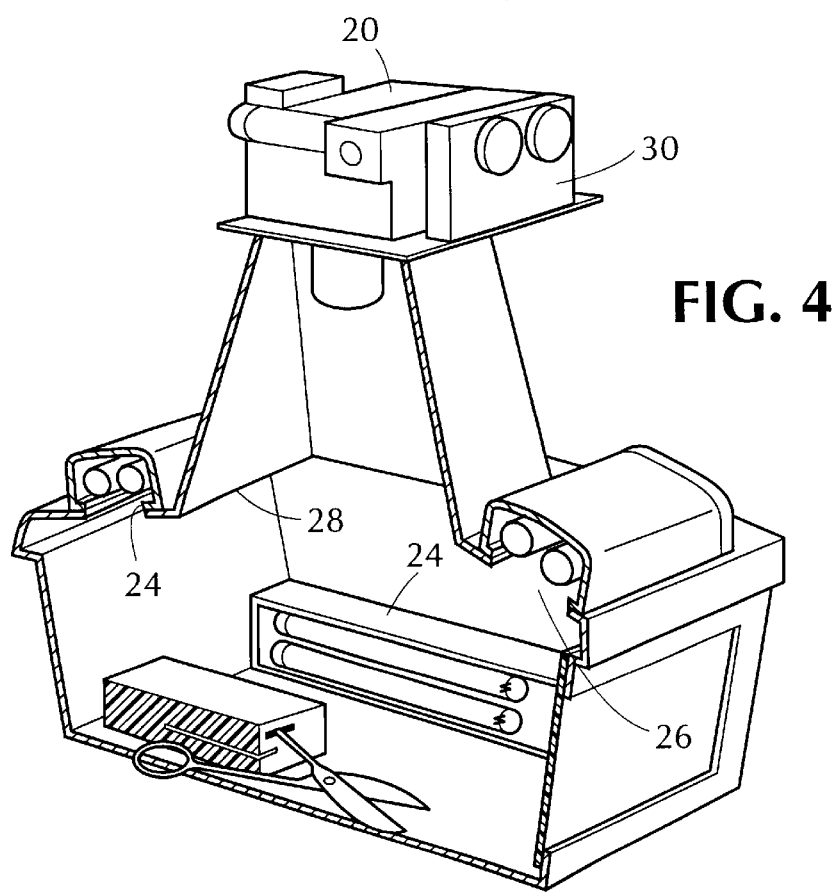
FIG. 4 is a sectional view taken along line 4—4 of FIG. 1.

The structure of visualization chamber 10 is illustrated in greater detail in FIG. 4. As seen therein the housing has openings 26 therein above which the ultraviolet fixtures 24 are mounted in any convenient manner.

Support 16 is mounted above an opening 28 in the housing in any convenient manner. Preferably the support 16 simply sits about the periphery of the opening.

Camera 20 is mounted on support 16 by a bracket 30 or the like.

Figure 3:
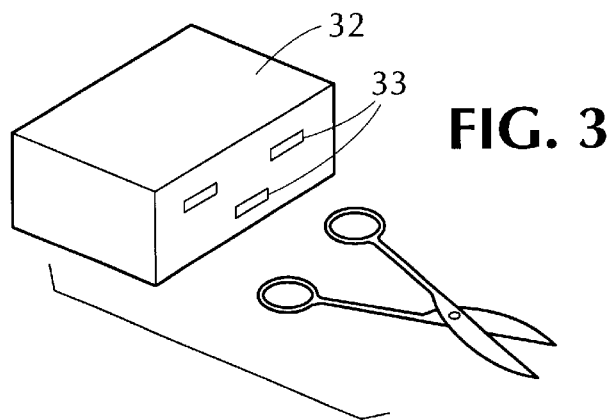
FIG. 3 is a perspective view of a mounting block for surgical instruments to be supported within the apparatus of FIG. 1.

The ultraviolet light fixtures 24 project light into the interior of the chamber towards a removable instrument mounting block 32. The mounting block may be formed in any convenient manner, for example, it may simply be a styrofoam block 32, as illustrated in FIG. 3, having a plurality of slots 33 formed therein which will frictionally retain a surgical instrument such as a scalpel, clamp, scissors or the like therein. Of course, other convenient mounting systems could also be used.

Figure 2:
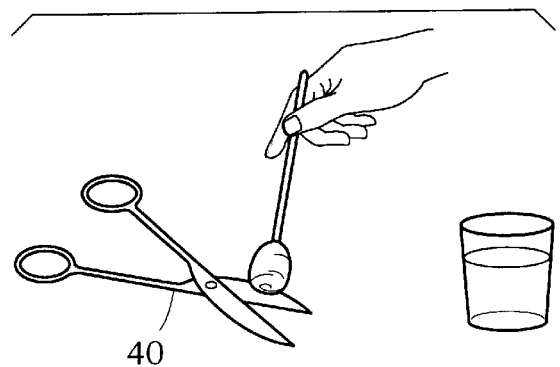
FIG. 2 is a perspective view of a technique for applying a visualization dye to a surgical instrument for use in the present invention.

As noted above, the present invention is intended for use in checking for the presence of, i.e., visualizing, bio-burden on a surgical instrument, whether before or after sterilization. To do so, the instrument is first bathed in a visualizing compound which can be one of a number of fluorescent substances, or combination of substances, that have the ability to fluoresce or phosphoresce when attached to a organic residue and subjected to ultraviolet light. An example of a surgical instrument 40 is illustrated in FIG. 2, as having an appropriate dye applied to it by a swab. Preferably the swab is used once so as not to contaminate other instruments. Alternative methods of applying the dye may also be used such as dipping, immersion, or spray.

Once the instrument is fully coated with the dye, it is mounted in block 32 in chamber 10 immediately beneath the camera 20. Ultraviolet lights 24 are then turned on and the instrument can be viewed through the camera or, if the camera is a CCD instrument, through a computer terminal 42 connected to the camera using known software. If there is bio-burden on the instrument, it will fluoresce and appear to the viewer, although the bio-burden would not necessarily visually be seen under normal light.

The following is a list of compounds that either alone or in combination can be used as the visualizing compounds for the material:

| UV | |
|---|---|
| | Chemical Abstract Service No. |
| Nile red | [7385-67-3] |
| Nile blue A | [3625-57-8] |
| Lucifer Yellow VS | [71231-14-6] |
| Lucifer Yellow CH | [67769-47-5] |
| Fluorescamine | [38183-12-9] |
| Fluorescent Brightener 28, Free Acid | [4404-43-7] |
| Lumichrome | [1086-80-2] |
| Diiodofluorescein | [31395-16-1] |
| Ethyl Eosin | [6359-05-3] |
| 8-Anilino-1-naphthalenesulfonic acid | [82-76-8] |
| Fluoresceinamine, isomer II | [51649-83-3] |
| Fluorescein diacetate | [596-09-8] |
| Fluoresceinamine, isomer I | [3326-34-9] |
| 3-aminophthalhydrazide | [521-31-3] |
| Eosin Y (Acid Red 87) | [548-26-5] |
| Fluorescein (Solvent Yellow 94) | [2321-07-5] |
| Fluorescein diacetate | [596-09-8] |
| 2',7'-diclolrofluorescein | [76-54-0] |
| Sulforhodamine B (Acid Red 52) | [3520-42-1] |
| Sulforhodamine 101 (Acid Chloride) | [82354-19-6] |
| Thioflavin S (Direct Yellow 7) | 1326-12-1] |
| Rhodamine B (Basic Violet 10) | [81-88-9] |
| Visable IR | |
| indocyanine green Indotricarbocyanine (ICC) | |

In certain circumstances, particularly with large instruments, a third ultraviolet light source 24 can be mounted within chamber 10 to project light horizontally in the chamber to further illuminate the instrument.

In a currently preferred embodiment, visualization chamber 10 may be a chamber such as the Chromata View viewing cabinet available under Model No. C-65 from Ultraviolet Products of Upland, Calif. The light sources may be conventional ultraviolet light fixtures which sit on the cabinet, and which produce ultraviolet light in the range of between 254 nm to 365 nm.

Preferably, the camera uses a 90 mm macro-lens in order to enable the viewer to obtain a one-to-one size image which is clearer and has a larger depth of field.

Figure 5:
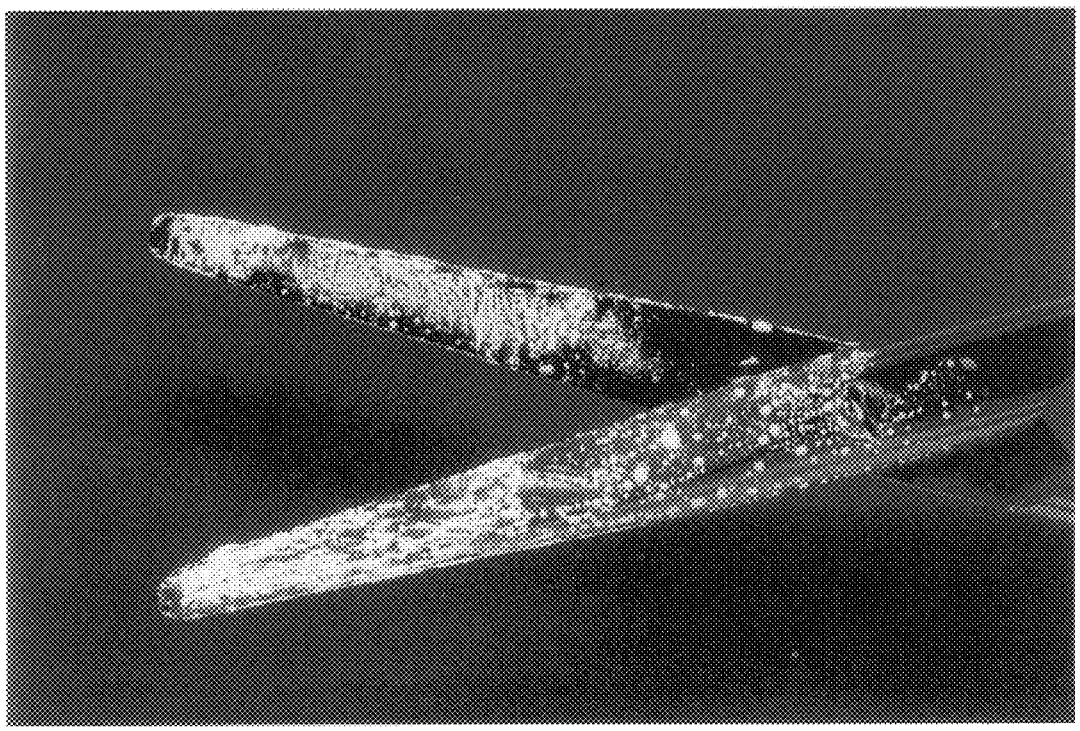
FIG. 5 is a photograph of an unclean surgical instrument viewed using the process of the invention.
Figure 6:
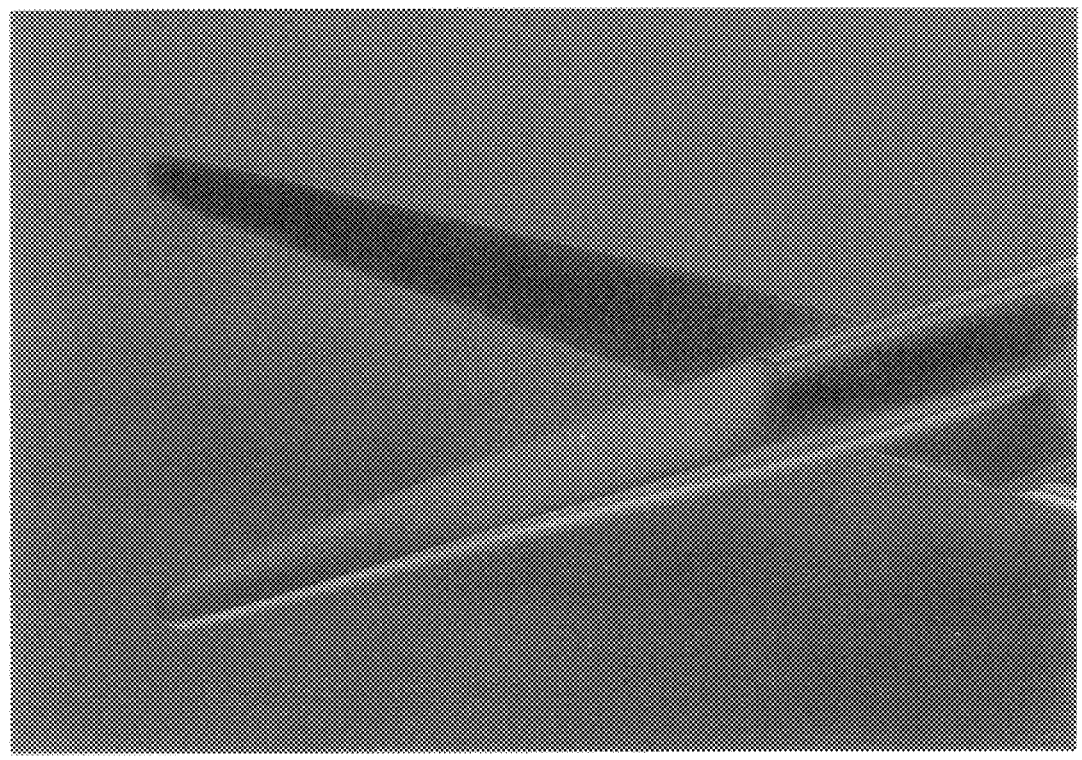
FIG. 6 is a photograph of the same instrument afer cleaning when viewed with the system of the present invention.
Figure 7:
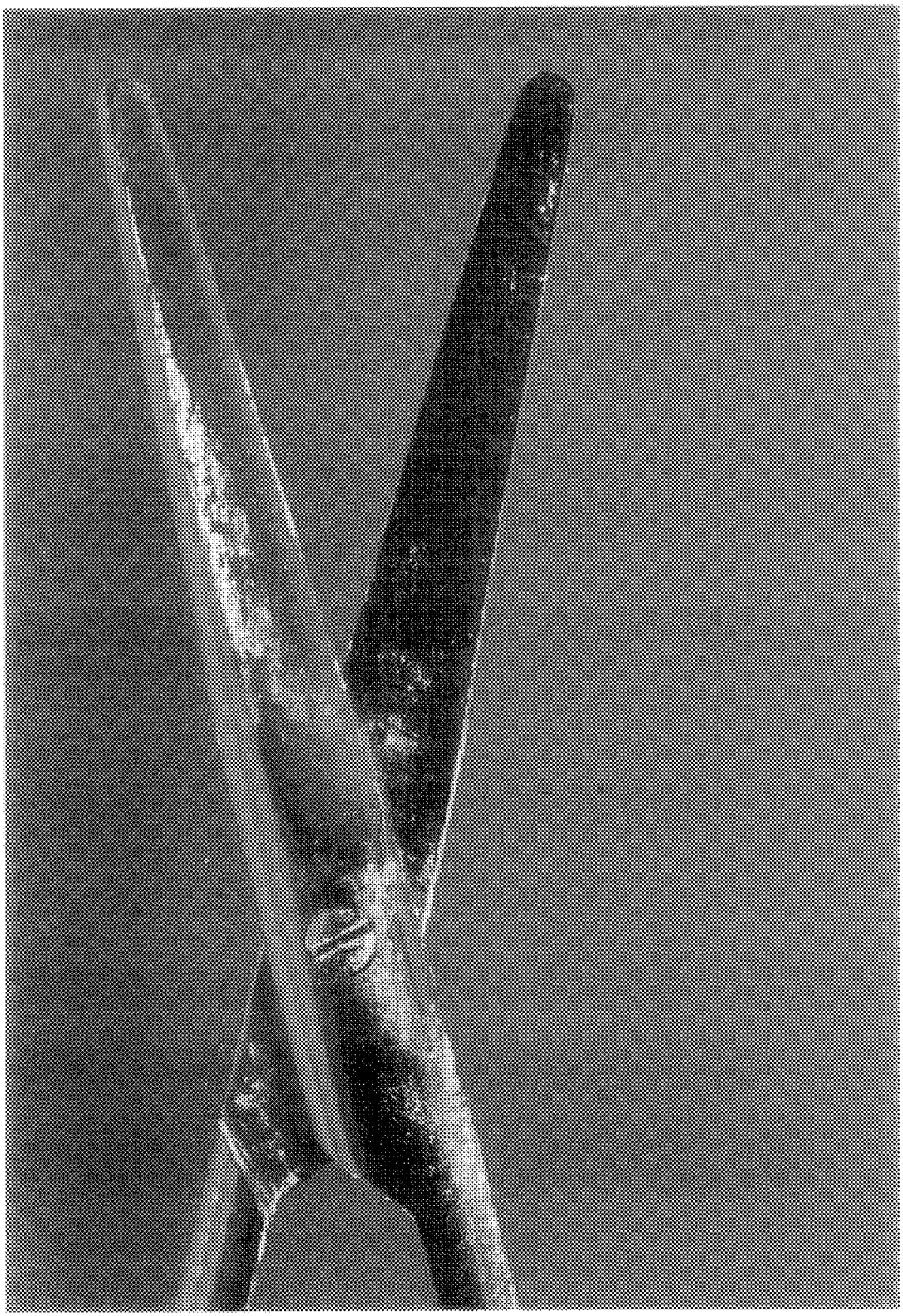
FIG. 7 is an instrument after cleaning when viewed with the system of the present invention with visualized bio-burden.

FIGS. 5 and 6 show the results of the process, wherein FIG. 5 shows a fluoresced surgical instrument carrying bio-burden and the bio-burden is shown as fluorescing on the instrument. FIG. 6 shows the same instrument after proper cleaning with no fluorescent material visible.

The system and method of the present invention could be used to visualize organic residues left on surgical and medical instruments after cleaning; or after sterilization, or in a training program to insure proper cleaning techniques or to check the efficacy of cleaning supplies.

Although an illustrative embodiment of the invention has been described herein with reference to the accompanying drawings, it is to be understood that various changes and modifications may be effected therein by those skilled in the art without the product and the scope or spirit of this invention.

What is claimed is:

1. A method of visualizing biological material on medical instruments comprising the steps of selecting a dye material capable of creating fluorescence when applied to biological material and subjected to ultraviolet light; applying said dye to a medical instrument; mounting said instrument in a viewing box; exposing the instrument in the viewing box to ultraviolet light; and observing said instrument through an opening in the viewing box to determine if said dye has caused fluorescence of material on the instrument indicative of the presence of biological material thereon; said step of exposing the medical instrument to ultraviolet light comprising the step of directing ultraviolet light on the instrument from at least two angularly related ultraviolet light sources located in the viewing box.

2. The method as defined in claim 1 wherein said observing step comprises the step of viewing the instrument with a camera.

3. The method as defined in claim 1 wherein said observing step comprises the step of using a digital CCD camera connected to a computer and computer monitor.

4. The method as defined in claim 1 wherein said step of directing ultraviolet light on the instrument includes locating the at least two light sources at a location above the instrument and adjacent the opening in the viewing box.

5. The method as defined in claim 4 wherein said step of directing ultraviolet light on the instrument includes the step of directing ultraviolet light from a third light source transversely of the at least two light sources.

6. The method as defined in claim 1 wherein said step of selecting a dye material comprises the step of selecting the dye from the group consisting of Nile red, Nile blue A, Lucifer Yellow VS, Lucifer Yellow CH, Fluorescamine, Fluorescent Brightener 28, Free Acid, Lumichrome, Diiodofluorescein, Ethyl Eosin, 8-Anilino-1-naphthalenesulfonic acid, Fluoresceinamine, isomer II, Fluorescein diacetate, Fluoresceinamine, isomer I, 3-aminophthalhydrazide, Eosin Y (Acid Red 87), Fluorescein (Solvent Yellow 94), Fluorescein diacetate, 2',7'-diclolrofluorescein, Sulforhodamine B (Acid Red 52), Sulforhodamine 101 (Acid Chloride), Thioflavin S (Direct Yellow 7), Rhodamine B (Basic Violet 10), indocyanine green and Indotricarbocyanine (ICC).

7. The method as defined in claim 1 wherein said step of applying the dye to the medical instrument comprises the step of swabbing the dye onto the instrument.

8. A method of visualizing a predetermined class of material on a medical instrument comprising the steps of selecting a dye material capable of creating fluorescence when applied to said predetermined class of material and subjected to ultraviolet light; applying said dye to a medical instrument; mounting the medical instrument in a viewing box; exposing the medical instrument in the viewing box to ultraviolet light; and observing said instrument through an opening in the viewing box to determine if said dye has caused fluorescence of material on the instrument indicative of the presence of said predetermined class of material thereon;

said observing step comprising the step of viewing the instrument with a camera; and said step of exposing the medical instrument to ultraviolet light comprises the step of directing ultraviolet light on the instrument from at least two angularly related ultraviolet light sources located in the viewing box.

9. The method as defined in claim 8 wherein said step of selecting a dye material comprises the step of selecting the dye from the group consisting of Nile red, Nile blue A, Lucifer Yellow VS, Lucifer Yellow CH, Fluorescamine, Fluorescent Brightener 28, Free Acid, Lumichrome, Diiodofluorescein, Ethyl Eosin, 8-Anilino-1-naphthalenesulfonic acid, Fluoresceinamine, isomer II, Fluorescein diacetate, Fluoresceinamine, isomer I, 3-aminophthalhydrazide, Eosin Y (Acid Red 87), Fluorescein (Solvent Yellow 94), Fluorescein diacetate, 2',7'-diclolrofluorescein, Sulforhodamine B (Acid Red 52), Sulforhodamine 101 (Acid Chloride), Thioflavin S (Direct Yellow 7), Rhodamine B (Basic Violet 10), indocyanine green and Indotricarbocyanine (ICC).

10. The method as defined in claim 9 wherein said viewing step comprises the step of using a digital CCD camera connected to a computer and computer monitor.

11. The method as defined in claim 10 wherein said step of directing ultraviolet light on the instrument includes locating the at least two light sources at a location above the instrument and below the opening in the viewing box.

12. The method as defined in claim 11 wherein said step of directing ultraviolet light on the instrument includes the step of directing ultraviolet light from a third light source transversely of the at least two light sources.

13. The method as defined in claim 12 wherein said step of applying the dye to the medical instrument comprises the step of swabbing the dye onto the instrument.

\* \* \* \* \*